(12) United States Patent
Kawai et al.

(10) Patent No.: US 6,434,214 B1
(45) Date of Patent: Aug. 13, 2002

(54) X-RAY CT APPARATUS AND X-RAY IMAGING METHOD

(75) Inventors: Hiroyuki Kawai, Tokyo; Kenichi Okajima, Mitaka, both of (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/869,899

(22) PCT Filed: Jan. 5, 2000

(86) PCT No.: PCT/JP00/00009
§ 371 (c)(1),
(2), (4) Date: Jul. 9, 2001

(87) PCT Pub. No.: WO00/41627
PCT Pub. Date: Jul. 20, 2000

(30) Foreign Application Priority Data

Jan. 11, 1999 (JP) ............................................. 11-003805

(51) Int. Cl.[7] ................................................. A61B 6/00
(52) U.S. Cl. ............................................. 378/4; 378/20
(58) Field of Search .......................................... 378/4, 20

(56) References Cited

U.S. PATENT DOCUMENTS 6,215,844 B1 * 4/2001 Adachi et al. ................. 378/19

FOREIGN PATENT DOCUMENTS

JP 2000-232977 * 8/2000 ............ A61B/6/03

* cited by examiner

*Primary Examiner*—David P. Porta
*Assistant Examiner*—Elizabeth Gemmell
(74) *Attorney, Agent, or Firm*—Antonelli, Terry, Stout & Kraus, LLP

(57) ABSTRACT

An X-ray CT apparatus includes a scanner mounted with a detection system having an X-ray source for generating X-rays applied radially to an object and a detector arranged so as to be opposite to the X-ray source and adapted to detect the image of the transmitted X-rays transmitted through the object, wherein the scanner is rotated around the object. A three-dimensional X-ray absorption coefficient distribution image of the object is reconstructed from the transmitted X-ray image and the rotation-axis projection position which is the position where the rotation center of the scanner is projected on the detection plane of a two-dimensional sensor constituting the detector is decided. On the basis of the contrast of the X-ray absorption coefficient distribution image reconstructed by using the decided rotation-axis projection position, the rotation-axis projection position is estimated, and an X-ray tomographic image or/and a three dimensional X-ray image of the object is generated.

13 Claims, 8 Drawing Sheets

X-RAY CT APPARATUS AND X-RAY IMAGING METHOD

TECHNICAL FIELD

The present invention relates to an X-ray computed tomography, and more particularly to the technique which is effectively applied to the positioning of a rotation center of a scanner of a detection system in a cone-beam X-ray computed tomography.

BACKGROUND ART

FIG. 6 is a view showing the general construction of a conventional cone-beam X-ray CT. The conventional cone-beam X-ray CT was divided into imaging unit 1 for carrying out the imaging and image processing unit 2 for processing the detected image data. Control unit 3 carries out the whole control for the imaging unit 1 and the image processing unit 2. In the imaging unit 1, an X-ray source 5 and a two-dimensional detector 6 were arranged in such a way as to be opposite to each other through an object. The X-ray source 5 and the two-dimensional detector 6 were both arranged in a scanner as a scanning mechanism which is rotated around an object 7 with a central axis 9 for the rotation as the rotation center.

The scanner 4 was rotated every predetermined angle and the two-dimensional detector 6 carries out the measurement of the intensity of the transmitted X-rays, which were transmitted through the object 7, every predetermined angle, thereby carrying out the imaging of the transmitted X-ray image of the object 7. The transmitted X-ray image which has been imaged by the two-dimensional detector was converted into the digital image data which was in turn outputted to the image processing unit 2. But, in the following description, the angle of rotation of the scanner 4 is referred to as a projection angle a.

In the image processing unit 2, first of all, the pre-processing such as the gamma correction, the distortion correction, the logarithmic transformation and the non-uniformity correction of the two-dimensional detector 6 were carried out in pre-processing means 10. Next, reconstruction means 11, on the basis of all of the transmitted X-ray images (all of the projected images) after completion of the pre-processing reconstructed the three-dimensional reconstructed image which is the three-dimensional X-ray absorption coefficient distribution within the field of view of the object 7. As for this reconstruction arithmetic operation method, there is known the cone-beam reconstruction arithmetic operation method or the like by Feldkamp described in an article of L. A. Feldkamp et al.: PRACTICAL CONE-BEAM ALGORITHM, Journal of Optical Society of America, A.Vol. 1, No. 6, pp. 612 to 619 (1984) (article 1).

Finally, imaging means 12 subjected the three-dimensional reconstructed image to the image processing such as the volume-rendering processing or the maximum-intensity-projection processing of displaying the resultant image in the form of the two-dimensional image on display means 13. At this time, on the basis of the parameters of a viewpoint, a region and the like to be observed which has been inputted through instruction means (not shown) such as a keyboard, a mouse and a track ball, the imaging means 12 executed the image processing.

In the conventional cone-beam X-ray CT, the scanner 4 mounted with the imaging system including the X-ray source 5 and the two-dimensional detector 6 was rotated and the transmitted X-ray image obtained around the object 7 was imaged, and the reconstruction means 11 obtained the three-dimensional X-ray absorption coefficient distribution of the object 7 placed on the stationary coordinate system fixed to the apparatus body. The stationary coordinate system was defined by the imaging system, i.e., the Z-axis as the rotation center 9 of the scanner 4, and the rectangular Cartesian coordinates on the plane on which the rotation orbit of an X-ray focus 14 of the X-ray source 5 lies (hereinafter, referred to as "a mid-plane" for short, when applicable), i.e., the X-axis and the Y-axis.

The position of an X-ray beam 8 imaged by the detection elements of the two-dimensional detector 6 was specified by an angle (projection angle) a between the straight line which passes through the orbit of the XYZ coordinate system for the X-ray focus 14 to reach the two-dimensional detector 6 and the X-axis, "the rotation-axis projection" which was obtained by projecting the rotation center 9 on an imaginary plane (projection plane) 15 is placed on the incident plane of the two-dimensional detector 6, and "the mid-plane projection" which is the straight line drew by the intersection between the mid-plane and the projection plane. That is, the coordinate axes, when reconstruction the three-dimensional X-ray absorption coefficient distribution of the object 7, were the rotation axis projection and the mid-plane projection on the projection plane.

Since for the actual imaging of the transmitted X-ray image, the continuous analog imaging is not carried out, but the discrete digital imaging is carried out, when performing the reconstruction arithmetic operation, the sampling pitch DP on the projection plane was also required. In addition, a distance SOD extending from the X-ray focus 14 to the rotation center 9, and a distance SID extending from the X-ray focus 14 to the rotation-axis projection 17 were both required. In the following description, the relative positional relationship among the X-ray focus 14, the two-dimensional detector 6 and the rotation center 9 will be referred to as "the geometry of the imaging system". The geometry of the imaging system is defined by the distance SOD extending from the X-ray focus 14 to the rotation center 9, and the distance SID extending from the X-ray focus 14 to the rotation-axis projection 17, the sampling pitch DP, the rotation-axis projection and the mid-plane projection on the projection plane 15.

It is well known that of the parameters by which the geometry of the imaging system is determined, the higher accuracy is required for the rotation-axis projection, the mid-plane projection and the sampling pitch than for the the distance SOD extending from the X-ray focus 14 to the rotation center 9, and the distance SID extending from the X-ray focus 14 to the 17 rotation-axis projection. For example, when the effective aperture width of the two-dimensional detector 6 is 30 cm, and the resolution thereof is 512×512 pixels, the accuracy of the rotation-axis projection, the mid-plane projection and the sampling pitch DP required 0.1 pixel, i.e., about 0.05 mm. This reason is that even if the fine error is present in the positions of the rotation-axis projection and the mid-plane projection, and the sampling pitch DP, the reduction of the image quality is provided for the reconstructed image.

It is known that of the positions of the rotation-axis projection and the mid-plane projection, and the sampling pitch DP, in particular, the rotation-axis projection is important, and even if the fine error is present, generates the remarkable artifact in the reconstructed image. On the other hand, it was difficult to image directly the positions of the rotation-axis projection and the mid-plane projection, and the sampling pitch DP. This reason resulted from the fact that the positions of the rotation-axis projection and the mid-plane projection, and the value of the sampling pitch DP depend on the characteristics of the two-dimensional detector 6 and the installation state of the apparatus.

As for a method of imaging the geometry of the imaging system with high accuracy, there was "the X-ray Tomographic Imaging System" described in JP-A-9-173330 (article 2) by the same applicant. In the X-ray tomographic imaging system described in the article 2, first of all, an object (phantom) 19 including a support member 20 and a corpuscle-shaped high absorption member 21 shown in FIG. 7 is arranged in the vicinity of a rotation center 9 (in the position which 3 cm to several centimeters a way from the rotation center 9), and the transmitted X-ray image thereof is imaged from the all-round direction. But, in the following description, the dedicated phantom 19, as shown in FIG. 7, which is used in the correction of the geometry of the imaging system will referred to as "the geometry estimate phantom" or "the phantom" for short.

If after completion of the necessary pre-processing such as the distortion correction and the non-uniformity correction, the transmitted X-ray images for all-round direction were added to each other, for example, as shown in FIG. 8, each of the corpuscle-shaped high absorption members 21 on the phantom 19 would draw an elliptical locus 23 on an added image 34. Since the straight line passing through the centers of the elliptical loci 23 becomes the rotation-axis projection 17 depending on the imaging conditions for the geometry estimate phantom 19, the position CP of the rotation-axis projection could be specified. On the other hand, the position MP of the mid-plane projection was obtained from the change in the length of the diameter in the direction of the rotation center (the minor axis of the elliptical locus 23). That is, the lengths of the minor axes of a plurality of imaged elliptical loci 23, and the positions of the rotation center directions thereof were expressed in the form of the graph, and the position where the length of the minor axis becomes zero was estimated, whereby the position MP of the mid-plane projection was obtained.

For the sampling pitch DP, first of all, for example, a metallic plate in which pin holes are bored at regular intervals, i.e., a hole chart or the like is stuck as a thin object having a predetermined length on the light receiving plane of the two-dimensional detector 6, i.e., the projection plane 15 to image one sheet of transmitted X-ray image. After the transmitted X-ray image had been subjected to the necessary pre-processing such as the distortion correction and the non-uniformity correction, with respect to how many pixels the image size or the hole part of the thin object corresponds to, the sampling pitch DP was obtained by comparison with the actual size.

DISCLOSURE OF THE INVENTION

The present inventors, as a result of examining the prior art, found out the following problems associated with the prior art. In the conventional X-ray CT, as described above, the estimation of the geometry of the imaging system required much work of an operator, for example, and much time. In particular, though the high accuracy was required with respect to the position CP of the rotation-axis projection, in the conventional geometry estimate method, the manipulation by an operator was required and hence there was a problem that a burden was imposed on an operator.

In addition, the accuracy which was obtained by the conventional method of estimating the geometry depended largely on a sense of an operator as a human being, and hence there was a problem that the sufficient accuracy could not be obtained by an operator. In addition, since the work of specification or the like of each of the central positions of the elliptical loci 23 was required, the estimation of the geometry of the imaging system took a lot of time and hence there was a problem that the reduced diagnostic efficiency was shown.

As for the method of solving the above-mentioned problems, the geometry estimation described in the article 2 can also be automatically carried out by executing the image recognition processing and the like. However, since in order to carry out the extremely accurate estimation, the complicated image processing needs to be performed, there is a problem that the manufacture cost of the apparatus is increased.

It is an object of the present invention to provide the technique which is capable of obtaining extremely accurately the position of the rotation-axis projection which contributes largely to the promotion of the high quality image of a reconstructed image and also to provide the technique which is capable of estimating parameters used to define the geometry of the imaging system without depending on a sense of an operator, the technique which is capable of estimating automatically parameters used to define the geometry of the imaging system, and the technique which is capable of improving the diagnostic efficiency.

The objects and novel features of the present invention will be apparent by reference to the description of the present specification and the accompanying drawings. Of the inventions disclosed herein, the typical ones are described as follows.

An X-ray CT according to the present invention includes: a scanner mounted with a detection system having an X-ray source for applying the radial X-rays to a object and imaging means arranged so as to be opposite to the X-ray source and adapted to detect a transmitted X-ray image of the X-rays transmitted through the object (phantom); rotation means for rotating the scanner around the object; reconstruction means for reconstructing a reconstructed image of the object from the transmitted X-ray image; initial-value decision means for deciding an initial value of the position of a rotation center (the position of a rotation-axis projection) of the scanner which is projected on the transmitted X-ray image, wherein the position of the rotation center of the scanner is estimated on the basis of the contrast of the three-dimensional X-ray distribution image which is reconstructed by changing the position of the rotation axis projection decided by the initial value decision means; and an X-ray tomographic image or/and an X-ray three-dimensional image of the object is/are generated from the reconstructed image, which is reconstructed by utilizing the estimated position of the rotation center, to be displayed.

In addition, an X-ray imaging method according to the present invention is an X-ray imaging method for obtaining an X-ray CT image, the method including: the step of collecting a transmitted X-ray image of X-rays transmitted through a object by a scanner mounted with detection means having an X-ray source for generating the X-rays applied radially to the object (phantom) and imaging means arranged so as to be opposite to the X-ray source; the step of deciding previously the position of the rotation-axis projection as the position which is obtained by projecting a rotation center of the scanner on a detection plane of a two-dimensional detector constituting imaging means; the step of reconstructing an X-ray absorption coefficient distribution image of the object from the transmitted X-ray image on the basis of the position of the rotation-axis projection; the step of estimating the position of the rotation-axis projection from the X-ray absorption coefficient distribution image thus obtained; the step of reconstructing a three-dimensional X-ray absorption coefficient distribution image of the object from the transmitted X-ray image; the step of generating an X-ray tomographic image or/and the three-dimensional X-ray image of the object from the three-dimensional X-ray absorption coefficient distribution image thus obtained; and the step of displaying the X-ray tomographic image or/and three-dimensional X-ray image thus obtained. For the estimation of the position of the rotation-axis projection, the position of the rotation-axis projection where the contrast of the X-ray absorption coefficient distribution image obtained from the transmitted X-ray image of the object shows a maximum or a local maximum is specified and estimated as the position of the rotation-axis projection on the transmitted X-ray image.

The property that if the reconstruction arithmetic operation is carried out in the state in which the position of the projected rotation center is deviated, since the artifact of arc shape is generated on the resultant reconstructed image, the contrast is reduced is utilized, and the position of the rotation-axis projection where the contrast of the reconstructed image shows a maximum is decided as the proper position of the rotation-axis projection. As a result, the position of the rotation-axis projection as the parameter used to define the geometry of the imaging system can be estimated using the value independent of a sense of an operator and called the contrast of the reconstructed image. Therefore, the position of the rotation-axis projection which contributes greatly the promotion of the high image quality of the reconstructed image can be obtained with high accuracy.

In addition, the contrast of the reconstructed image is decided as the parameter used to define the geometry of the imaging system, whereby it becomes possible to define the function of the contrast of the reconstructed image in which the projected rotation center is treated as the variable. Therefore, it is possible to estimate automatically the position of the projected rotation center as the parameter used to define the geometry of the imaging system. As a result, a time required to estimate the geometry of the imaging system, i.e., a time required to adjust the X-ray CT can be reduced and hence the diagnostic efficiency can be reduced.

The effects offered by the typical ones of the inventions disclosed herein are simply described as follows. (1) The position of the rotation-axis projection which contributes greatly to the promotion of the high image quality of the three dimensional X-ray absorption coefficient distribution image can be obtained with high accuracy. (2) The parameters used to define the geometry of the imaging system can be estimated independently of a sense of an operator. (3) The parameters used to define the geometry of the imaging system can be automatically estimated. (4) The diagnostic efficiency can be enhanced.

The typical construction of the present invention is summarized as follows with reference to FIG. 1. An X-ray CT includes: a scanner which is mounted with an imaging system having an X-ray source for applying the radial X-rays to a object and imaging means arranged so as to be opposite to the X-ray source and adapted to detect a transmitted X-ray image of the X-rays transmitted through the object; rotation means for rotating the scanner around the object; reconstruction means for reconstructing a reconstructed image of the object from the transmitted X-ray image; and decision means for deciding the position of the rotation-axis projection as the position which is obtained by projecting the rotation center of the scanner on a detection plane of a two-dimensional X-ray detector constituting the imaging means, wherein the position of the rotation-axis projection of the scanner is estimated on the basis of the contrast of a reconstructed image which is reconstructed by using the rotation-axis projection decided by the decision means, and an X-ray tomographic image or/and an X-ray three-dimensional image of the object is/are generated from the reconstructed image which is reconstructed in the position of the estimated rotation-axis projection to be displayed. According to the present invention, the position of the rotation-axis projection which contributes greatly to the promotion of the high image quality of the three-dimensional absorption coefficient distribution image can be estimated with high accuracy.

BEST MODE FOR CARRYING OUT THE INVENTION

Figure 1:
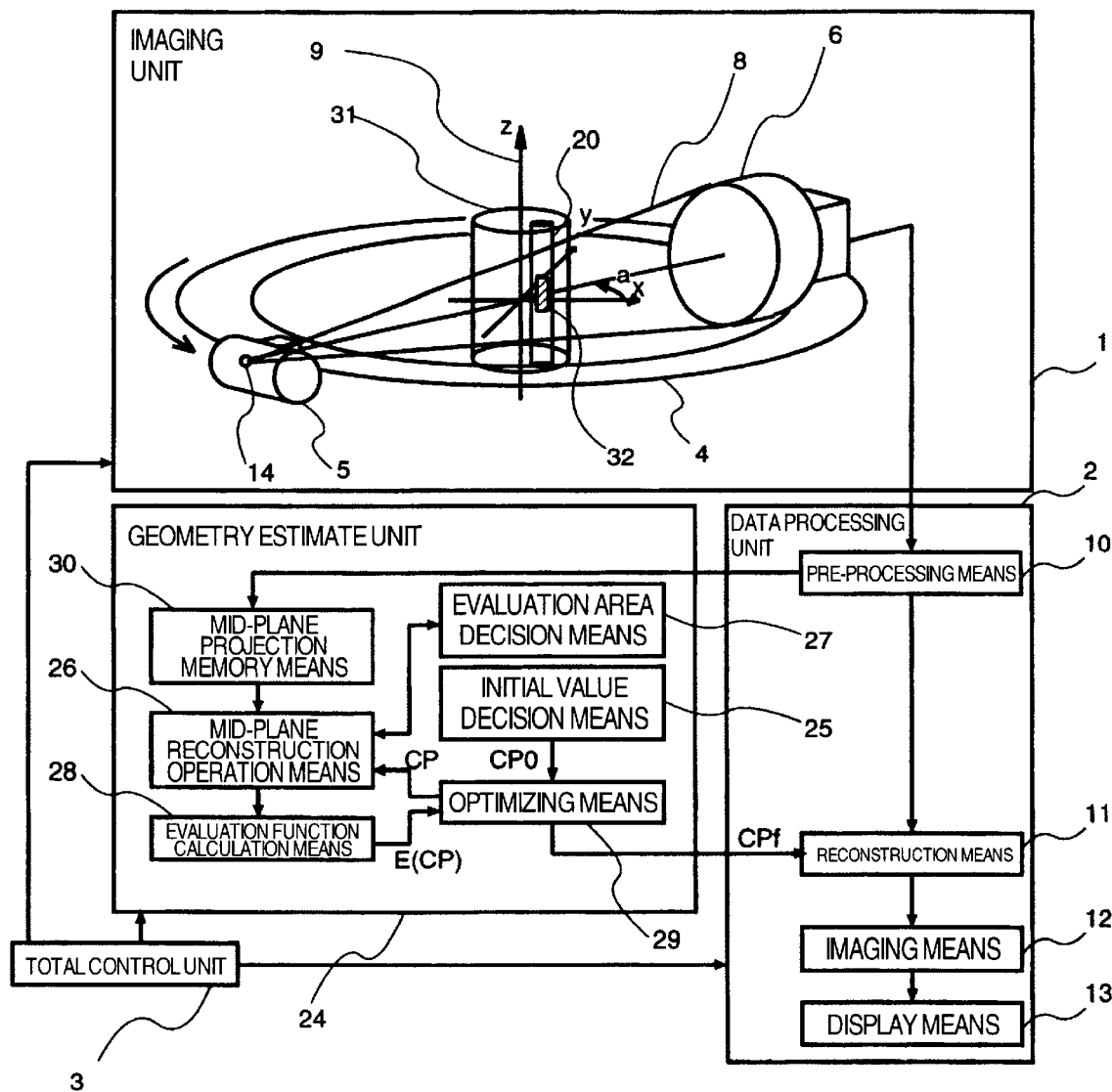
FIG. 1 is a view showing the schematic construction of a cone-beam X-ray CT as an X-ray CT of an embodiment 1 of the present invention.

Embodiments of the present invention will hereinafter be described with reference to the accompanying drawings. By the way, in all of the drawings explaining embodiments of the present invention, constituent elements having the same functions are designated with the same reference numerals, and the repeated description thereof is omitted here.

EMBODIMENT 1

FIG. 1 is a view showing the schematic construction of a cone-beam X-ray CT as an X-ray CT of an embodiment 1 of the present invention. The cone-beam X-ray CT of an embodiment 1 includes imaging unit 1 for imaging a transmitted X-ray image obtained around an object 7, image processing unit 2 for carrying out the image reconstruction from the imaged X-ray intensity image, and geometry estimate means (estimate means, and decision means for deciding the position of the rotation axis projection) for estimating the geometry of an imaging system. In addition, the cone-beam X-ray CT includes also control unit 3 for carrying out the whole control for the imaging unit 1, the image processing unit 2 and the geometry estimate unit 24. But, the imaging unit 1 has the same construction as that of the conventional one and includes a scanner (a rotating disc having a hollow central portion) 4 which is mounted with a detection system having an X-ray source 5 for radiating the cone-beam-like X-rays, a two-dimensional X-ray detector (imaging means) 6 for imaging the transmitted X-ray image of the X-rays transmitted through an object 7, 31 to be imaged which is arranged in the vicinity of a rotation center 9, and the X-ray source 5 which is arranged in such a way as to be opposite to the detector 6. The scanner is rotated around the rotation center 9 by rotation means (not shown). Next, the description will hereinbelow be given with respect to the processing executed in each of the constituent means and the flow of the data transmitted between the constituent means on the basis of FIG. 1. But, the details of the individual processings will be described later.

The image processing unit 2 includes pre-processing means 10, reconstruction arithmetic operation means (reconstruction means) 11, imaging means 12 and display means 13. But, since the reconstruction means 11, the imaging means 12 and the display means 13 other than the pre-processing means 10 have the same configurations as those of the conventional cone-beam X-ray CT, the detailed description thereof is omitted here. In the normal reconstruction, similarly to the conventional pre-processing means, the pre-processing means 10 subjects the imaged image data to the necessary pre-processing such as the gamma correction, the distortion correction, the logarithmic transformation and the non-uniformity correction. On the other hand, in the estimation of the geometry of the imaging system, the pre-processing means 10, only for the previously specified area, subjects the imaged image data to the necessary pre-processings such as the gamma correction, the distortion correction, the logarithmic transformation and the non uniformity correction. The previously specified area, for example, is set to the minimum area which is required to generate the projected image corresponding to the mid-plane projection (hereinafter, referred to as "the mid-plane area" for short, when applicable), whereby it is possible to reduce a time required to estimate the Geometry of the imaging system. By the way, its details will be described later.

The pre-processing means 10 of the embodiment 1 can be constituted by first pre-processing means for subjecting the whole range of the imaged image data to the pre-processing in the normal reconstruction, and by second pre-processing means for subjecting only the mid-plane area of the imaged image data to the pre-processings in the automatic estimation of the position CP of the rotation-axis projection.

Geometry estimate unit 24 includes initial-value decision means (initial-value memory means) 25 for deciding an initial value of the position of the rotation-axis projection, mid-plane reconstruction means (partial reconstruction means) 26, evaluation-area decision means 27, evaluation-function calculation means 28 and optimizing means 29, and in particular, carries out the estimation of the position CP of the rotation axis projection of the geometry.

The initial-value decision means 25 for deciding an initial value of the position of the rotation-axis projection is the means for obtaining an initial value CP0 of the position CP of the rotation-axis projection. The initial-value decision means 25 of the embodiment 1 outputs as the initial value CP0 the coordinate value at the center of the width in the direction of the rotating tangential line of the projected image, i.e., the coordinate value at the center of the aperture width of the detector 6. The initial-value decision means 25 outputs the resultant initial value CP0 to the optimizing means 29.

The mid-plane reconstruction means 26 is the arithmetic operation means for carrying out the reconstruction arithmetic operation using the estimated value of the position CP of the rotation-axis projection specified by the optimizing means 29 to obtain a tomographic image on the mid-plane 16 (hereinafter, referred to as "a mid-plane image" for short, when applicable). In the embodiment 1, the mid-plane reconstruction means 26 does not simply reconstruct the whole plane of the mid-plane, but reconstructs only the pre-decided area or the evaluation area decided by the evaluation-area decision means 27. The procedure of deciding the evaluation area by the evaluation area decision means 27 will be described later.

While the embodiment 1 is constructed in such a way that the mid-plane reconstruction means 26 obtains the mid-plane image, it is to be understood that the present invention is not intended to be limited thereto, and for example, the reconstruction means 11 for carrying out the normal reconstruction arithmetic operation may be employed as the mid plane reconstruction means 26. In the case where the reconstruction means 11 is employed as the mid-plane reconstruction means 26, the reconstruction means 11, when carrying out the normal reconstruction, reconstructs the whole area of the reconstruction area specified by an operator, and when executing the geometry estimate processing, reconstructs only the mid-plane cross section image, the pre-decided area or the evaluation area decided by the evaluation-area decision means 27.

The evaluation-area decision means 27 is the means for when executing the estimate processing for the position CP of the rotation-axis projection, deciding the evaluation area becoming an object of the evaluation of the evaluation function. In the embodiment 1, in order that the burden imposed on an operator may be reduced and also the automatic estimation for the position of the rotation center may be stably carried out, the evaluation-area decision means 27 carries out the automatic decision of the evaluation area. But, the evaluation area either may be previously decided or may be specified on the basis of the initially reconstructed image by an operator.

When utilizing the rotation-axis projection position estimate phantom 31 for estimating the projected position of the rotation center, only the periphery of the region in which the reconstructed image of the material having the high absorption for the X-ray of the phantom 31 is present can be decided as the evaluation area. Then, the whole area of the mid-plane cross section or the area within the range in which it is ensured that the reconstructed image of an insert 32 having the high absorption for the X-ray of the phantom 31 is surely present on the mid-plane cross section is reconstructed on the basis of the initial value CP0 of the position of the rotation axis projection. Since in this stage, the initial value CP0 does not correspond to the proper position of the rotation axis projection, the artifact is contained in the mid-plane reconstructed image and hence the contrast is generally low. However, even if it is assumed that the region showing a maximum value of the reconstructed image is present in the vicinity of the region having the reconstructed image of the insert 32 having the high absorption for the X-ray of the phantom 31, there is no problem practically. In this connection, a maximum value of the CT value of the reconstructed image can be used as the contrast.

Therefore, in the embodiment 1, a predetermined area, containing the point at which the maximum value is taken, or having as the center the point at which the maximum value is taken, of the mid-plane image which has been reconstructed using the initial value CP0 is treated as the evaluation area, whereby the subsequent optimizing arithmetic operation can be carried out.

The evaluation-function calculation means 28 is the means for evaluating the mid-plane tomographic image present in the evaluation area to obtain an evaluation function E(CP). The evaluation-function calculation means 28 delivers the evaluation function E(CP) thus obtained to the optimizing means 29. But, the evaluation function E(CP) will be described later.

The optimizing means 29 is the means for controlling the flow of the processing of estimating the position CP of the rotation-axis projection. The optimizing means carries out the decision and the update of the estimated value for the position CP of the rotation-axis projection, and delivers the estimated value for the position CP of the rotation-axis projection to the mid-plane reconstruction means 26. In addition, the optimizing means 29 receives the evaluation function (CP) for the estimated value for the position CP of the rotation-axis projection obtained by the evaluation-function calculation means 28. The optimizing means 29 records the change in the evaluation function E(CP) in relation to the change in the estimated value for the position CP of the rotation-axis projection, and on the basis of a trend of the change in the evaluation function E(CP), updates the estimated value for the position CP of the rotation-axis projection to judge whether the processing of estimating the position CP of the rotation-axis projection should be carried out or the processing of estimating the position CP of the rotation-axis projection should be ended. Finally, the optimizing means 29 outputs as an optimized value CPf the value of the position CP of the rotation-axis projection where the evaluation function E(CP) shows a maximum value within a predetermined range of the error to deliver the optimized value CPf thus outputted to the image processing means 2. In this stage, the processing of estimating the position CP of the rotation-axis projection is ended. Subsequently, in the image processing means 2, the reconstruction processing is executed using the optimized value CPf of the position CP of the rotation axis projection.

Figure 2:
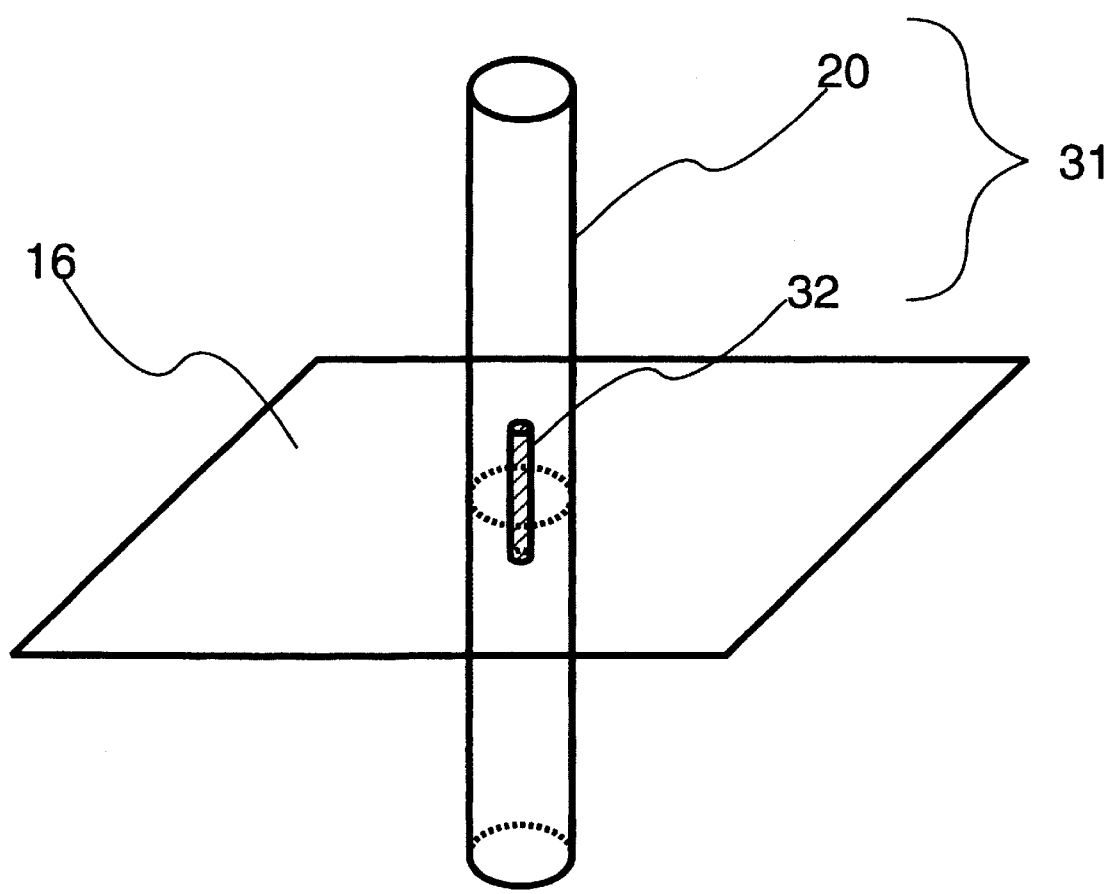
FIG. 2 is a view useful in explaining the schematic construction of a phantom of the embodiment 1 of the present invention.

FIG. 2 shows the phantom in the embodiment 1, in articular, the dedicated phantom 31 which is suitable for the automatic estimation of the position CP of the rotation-axis projection (hereinafter, referred to as "the position estimate phantom of the rotation-axis projection" or "the phantom" for short, when applicable). In FIG. 2, reference numeral 20 designates a support member, reference numeral 32 designates an insert, and reference numeral 31 designates a body of the phantom. But, the phantom 31 is also claimed by the present invention. The phantom 31 has the construction in which the insert 32 made of a material having high absorption for the X-ray is embedded in the support member 20 having low absorption for the X-ray. The support member 20 is formed into a stick made of a material having a small X-ray absorption coefficient such as a plastic material or polymeric resin including acrylate resin, vinyl chloride, polycarbonate or the like, or material, typified by wood, through which the X-ray is transmitted and which has the high strength against the mechanical destruction. The insert 32 is the columnar body with a predetermined length which is made of a material having a large X-ray absorption coefficient such as tungsten, platinum or an iron-nickel-chromium series alloy, and is formed into a wire or a stick.

The phantom 31 is preferably constructed in such a way that the insert 32 which is made of an iron-nickel-chromium series alloy and which is formed into a stick having a diameter of about 0.5 mm to about 1 mm is embedded along the axial direction of the stick-shaped support member 20 having a diameter of about 1 cm. In addition, since the insert 32, when installing the phantom 31 in the vicinity of the rotation center 9, needs to be set so as to cross the mid-plane, the insert 32 needs to have the length which is roughly equal to or longer than can be set with the naked eye. But, it is to be understood that the materials for the support member 20 and the insert 32 may be any of materials other than the above-mentioned materials as long as the desired contrast is obtained. Moreover, the support member 21 is provided in order to prevent the deformation or the like of the insert 32, or in order, to make easy the installation of the phantom in a predetermined position. Therefore, it is to be understood that even when only the insert 32 is provided for the phantom 31, it may also be available.

Since in the phantom 31 of the embodiment 1, the insert 32 having the high absorption for the X-ray is formed into a wire or a stick, when reconstructed in the form of the mid plane cross section, its reconstructed image shows a point and hence the evaluation of the contrast becomes easy. In addition, since when set in a predetermined position, the phantom 31 extends with a predetermined length along the direction which is roughly parallel to the rotation center 9, even if the phantom 31 is slightly deviated in the direction of the rotation center in the installation thereof, the deviation does not exert an influence on the reconstructed image when carrying out the imaging. That is, since the phantom is made of the above-mentioned material and also has the above-mentioned shape, the imaging and the evaluation of the contrast become easy to be carried out.

In addition, if the phantom 31 of the embodiment 1 is utilized, then the evaluation area can be further restricted. That is, the whole area of the mid-plane cross section for which the reconstruction arithmetic operation can be carried out does not need to be reconstructed, and hence only the periphery of the region in which the constructed image of the insert 32 having the high absorption for the X-ray of the phantom is present on the mid-plane cross section has only to be reconstructed. Since the area to be reconstructed is restricted to a minimum, it is not influenced by the region, which is inconvenient for the evaluation of the contrast, of a part constituting the phantom 31. By the part constituting the phantom is, for example, meant the jigs, the screws or the like for supporting the phantom 31. In addition, if the evaluation area is restricted, then the reconstruction arithmetic operation volume may also be a necessary minimum. As a result, the evaluation of the contrast can be carried out under the more stable condition. As described above, the phantom 31 is utilized in the estimation of the geometry of the imaging system, whereby the evaluation of the contrast becomes easy on the reconstructed image.

Figure 3:
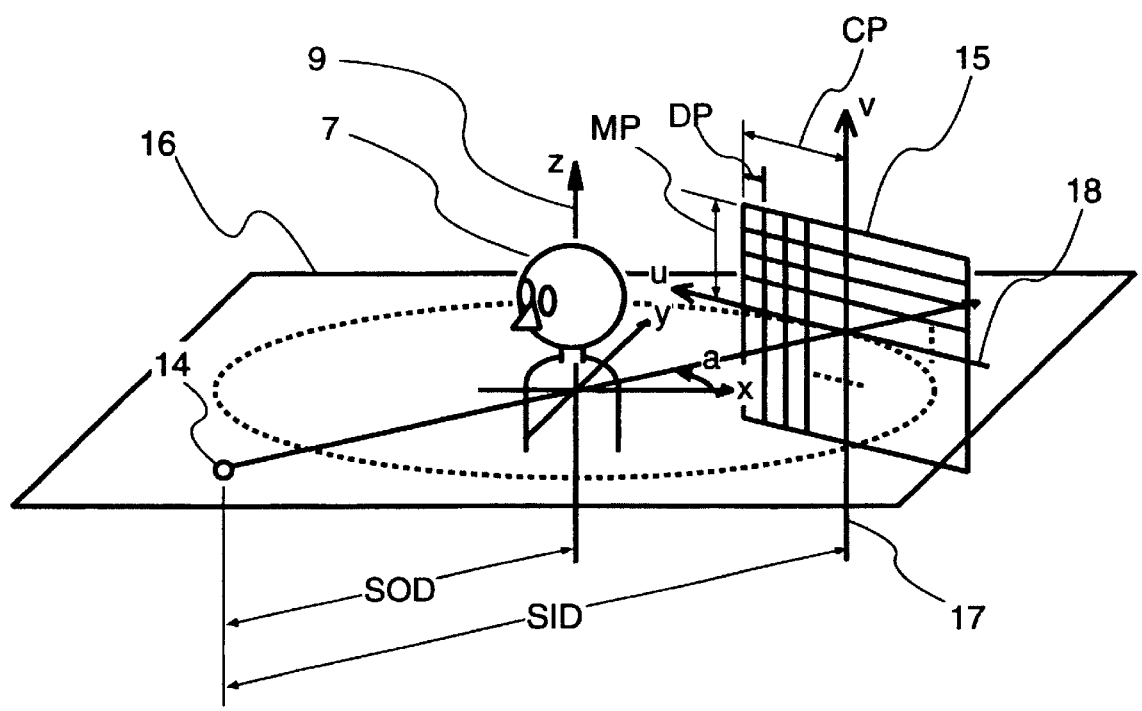
FIG. 3 is a view useful in explaining the geometry of an imaging system as the relative positional relationship among an X-ray focus, a two-dimensional detector and a rotation center.

Next, a view useful in explaining the relative positional relationship among the X-ray focus 14, the two-dimensional detector 6, and the rotation center 9, i.e., and the geometry of the imaging system, and the geometry of the imaging system will hereinbelow be described with reference to FIG. 3. But, in the following description, the constituent elements of the imaging system are abstracted, and the imaginary plane is placed in the position of the two-dimensional detector 6, and this plane is referred to as the projection plane. The plane on which the rotation orbit of the X-ray focus 14 lies is the mid-plane 16, and the straight line which is formed by projecting the rotation center 9 on the projection plane 15 is the rotation axis projection 17. The straight line which is formed by the projecting the mid-plane on the projection plane 15, i.e., the line of intersection between the mid-plane 16 and the projection plane 15 is the mid-plane projection 18.

The geometry of the imaging system is defined by a distance SID between the X-ray focus 14 and the projection plane 15, a distance SOD between the X-ray focus 14 and the rotation center 9, the position CP of the rotation-axis projection on the projection plane 15, and the position MP of the mid-plane projection. In addition, since in the actual imaging, the discrete imaging is carried out, when carrying out the reconstruction arithmetic operation, a sampling pitch DP on the projection plane 15 is also required. As described above, with respect to the distance SID between the X-ray focus 14 and the projection plane 15, and the distance SOD between the X-ray focus 14 and the rotation center 9 of the parameters used to decide the geometry, even if the error is slightly contained therein, the image quality of the reconstructed image which is finally obtained is not remarkably reduced. Therefore such parameters can be directly measured after completion of the assembly of the apparatus. Or, the apparatus is assembled within the range of the mechanical error specified in the designing stage, whereby the distances SID and SOD can be determined.

On the other hand, with respect to the position CP of the rotation-axis projection, the position MP of the mid-plane projection and the sampling pitch DP, the higher accuracy is required as compared with the distances SID and SOD. For example, if the effective aperture width of the detector 6 is 30 cm and the resolution is 512×512 pixels, for the CP, MP and DP, the accuracy of the 0.1 pixel, i.e., about 0.05 mm is required. This requirement results from the fact that even if the fine error is present in the position CP of the rotation-axis projection, the position MP of the mid-plane projection and the sampling pitch DP, the reduction of the image quality is provided in the reconstructed image. In particular, the position CP of the rotation-axis projection of the geometry of the imaging system, is important, and thus even if the fine error is present therein, the remarkable artifact is generated in the reconstructed image. However, it is difficult to measure directly these values. This results from the fact that the values of the position CP of the rotation-axis projection, the position MP of the mid-plane projection and the sampling pitch DP depend on the characteristics of the detector 6 and the installation state of the apparatus.

Figure 4:
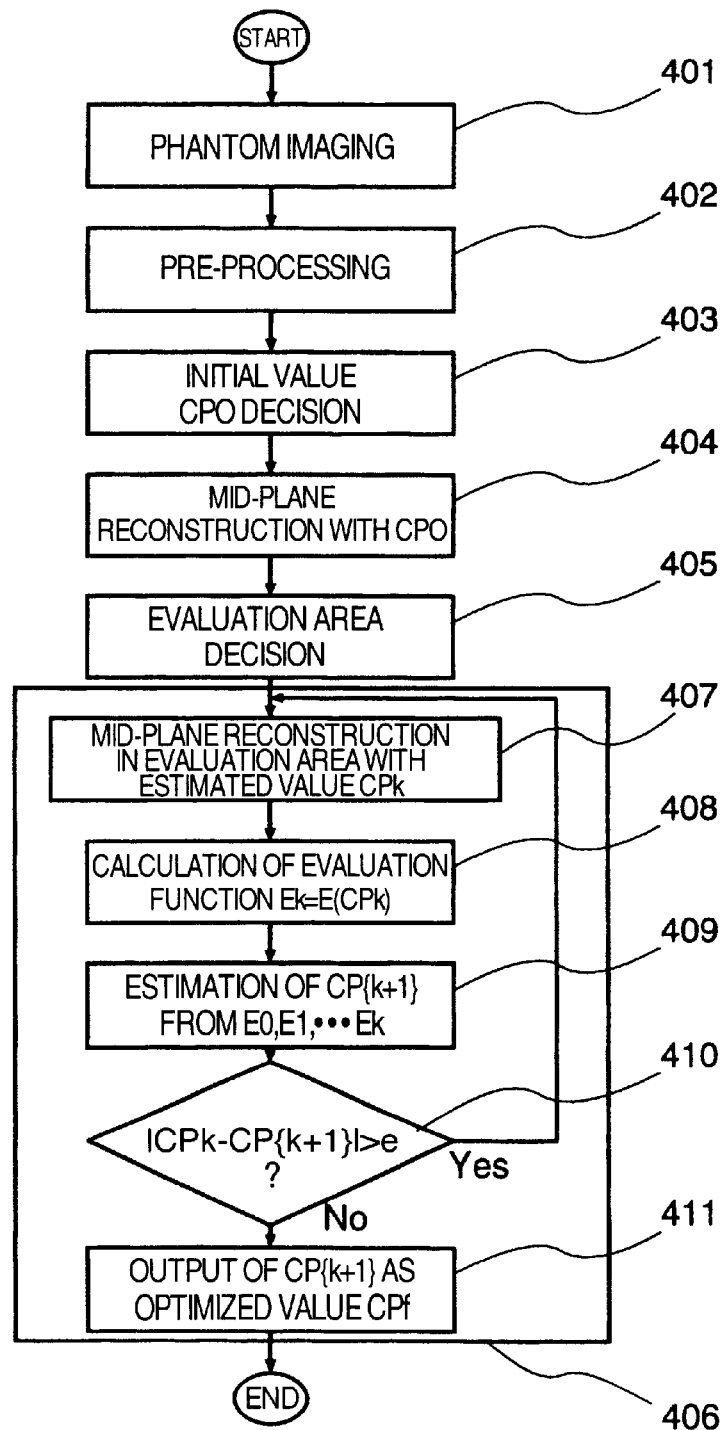
FIG. 4 is a flow chart useful in explaining the procedure of estimating the geometry of the imaging system by the cone beam X-ray CT of the embodiment 1.

Next, the flow useful in explaining the procedure of estimating the geometry of the imaging system by the cone-beam X-ray CT of the embodiment 1 is shown in FIG. 4. The operation of estimating automatically the geometry of the imaging system by the cone-beam X-ray CT of the embodiment 1 will hereinbelow be described on the basis of the flow shown in FIG. 4. But, since both of the mid-plane 16 and the mid-plane projection 18 are the same as those in the prior art, the detailed description thereof is omitted here.
(Step 401)

First of all, the phantom 31 is installed in a predetermined position to carry out the cone-beam imaging to collect the transmitted X-ray image (imaged image data) obtained by the rotation made around the object.
(Step 402)

Next, the pre-processing means 10 subjects the imaged image data obtained by the rotation made around the object to the necessary pre-processing such as the gamma correction, the distortion correction, the logarithmic transformation and the non-uniformity correction to generate the projected image. At this time, only the data within the region required to generate the projected image on the position of the mid-plane projection has only to be subjected to the pre-processings.
(Step 403)

The initial-value decision means 25 decides the initial value CP0 of the position CP of the rotation-axis projection.

As the initial value CP0, for example, the coordinate at the central position of the aperture width of the detector 6 is employed.
(Step 404)

The mid-plane reconstruction means 26 reconstructs the mid-plane tomographic image or a predetermined area on the mid-plane by utilizing the initial value CP0.
(Step 405)

The evaluation-area decision means 27 detects the pixel position showing a maximum on the mid-plane tomographic image obtained in Step 404 to set as the evaluation area the area containing that position or the area within a predetermined range with that position as the center.
(Step 406)

The reconstruction of the evaluation area and the calculation of the evaluation function are repeatedly carried out to perform the optimization within the range of a predetermined error e to estimate the position CP of the rotation-axis projection. But, the meaning of the optimization is to obtain the position CP of the rotation-axis projection where the evaluation function E(CP) shows a maximum, i.e., to obtain the optimized value CPf. More specifically, the optimization is carried out as follows.
(Step 407)

The evaluation area on the mid-plane is reconstructed with the estimated value CPk as the position of the rotation-axis projection to obtain the mid-plane tomographic image.
(Step 408)

For the mid-plane tomographic image obtained in Step 407, an evaluation function Ek=E(CPk) is obtained.
(Step 409)

The position CP of the rotation-axis projection where the evaluation function E(CP) shows a maximum is estimated from the series of E0, E1, E2, . . . , Ek to be decided as CP{k+1}.
(Step 410)

When (Expression 1) is fulfilled with e as a pre-set error, k is incremented to (k+1) using the estimated value CP {k+1} to execute repeatedly Step 407 to Step 410.

$$|CPk-CP\{k+1\}|>e \qquad \text{(Expression 1)}$$

On the other hand, when (Expression 2) is fulfilled, the processing proceeds to next Step 411.

$$|CPk-CP\{k+1\}|\leq e \qquad \text{(Expression 2)}$$

(Step 411)

CP{k+1} is outputted as the optimized value CPf.

The foregoing is the flow of the automatic estimation of the position CP of the rotation-axis projection utilizing the cone-beam X-ray CT of the embodiment 1 as the typical embodiment of the present invention.

In the cone-beam X-ray CT of the embodiment 1, the reconstruction arithmetic operation is carried out in the reconstruction means 11 using the optimized value CPf of the position CP of the rotation-axis projection which has been estimated on the basis of the estimate processing shown in Step 401 to Step 411. The procedure of estimating the rotation-axis projection using the transmitted X-ray image of the phantom 31 in the X-ray CT of the embodiment 1 is as follows.

The estimate procedure includes: the step of collecting the detected image data as the transmitted X-ray image (Step 401); the step of subjecting the imaged image data to the pre-processing correction (Step 402); the step of determining the initial value CP0 of the position CP of the rotation-axis projection by the initial-value decision means 25 (Step 403); the step of on the basis of the rotation center position pre-set by the initial-value decision means 25, reconstructing the mid-plane tomographic image of a object from the imaged image data by the mid-plane reconstruction means 26 (Step 404); the step of specifying the position, where the contrast of the mid-plane tomographic image is increased, as the rotation center position of the detection system projected on the transmitted X-ray image (i.e., the rotation center position of the scanner); the step of deciding as the evaluation area the area containing the maximum value pixel position or the area having the maximum value pixel position as the center by the evaluation-area decision means 27 (Step 405); the step of carrying out repeatedly the reconstruction of the evaluation area and the calculation of the evaluation function to carry out the optimization within the range of the predetermined error e to estimate the position CP of the rotation-axis projection (Step 406); the step of generating the X-ray tomographic image or/and the X-ray three-dimensional image from the reconstructed image reconstructed using the estimated position CP of the rotation-axis projection; and the step of displaying the X-ray tomographic image or/and the X-ray three-dimensional image which has/have been generated.

In addition, while in the imaging unit 1 of the cone-beam X-ray CT of the embodiment 1, there is adopted the construction in which the object 7 is fixed to a bedstead (not shown), and the scanner 4 mounted with the X-ray source 5 and the detector 6 are rotated around the object 7, the imaging unit 1 may have the construction other than the above-mentioned one. For example, there is conceivable the cone-beam X-ray CT including the imaging unit 1 having the construction in which both of the X-ray source 5 and the two-dimensional detector 6 are fixed by a supporting arm (not shown) or the like and in the imaging, the object 7 is rotated. In this case, since it becomes possible to change readily the geometry of the imaging system, the automatic estimation of the position of the rotation-axis projection according to the present invention is more effective.

(Estimate Arithmetic Operation of Position CP of Rotation-Axis Projection)

Next, the description will hereinbelow be given with respect to the estimate arithmetic operation of the position CP of the rotation-axis projection which is employed in the cone-beam X-ray CT of the embodiment 1. First of all, the basic principles of estimating automatically the position CP of the rotation center which is realized by the present invention will now be described. In general, it is known that if the reconstruction arithmetic operation is carried out with the position CP of the rotation-axis projection deviated, then artifact of arc shape is generated in the resultant reconstructed image, and also the contrast is reduced. That is, when the reconstruction arithmetic operation is carried out using the proper position CPp of the rotation-axis projection, the contrast of the reconstructed image becomes a maximum.

Therefore, in the present invention, the position CP of the rotation-axis projection where the contrast of the reconstructed image becomes a maximum is obtained, whereby the proper position CPp of the rotation-axis projection is calculated. To put is concretely, the position CP of the rotation center is made a variable, and the reconstructed tomographic image within a predetermined concern area is reconstructed using the position CP of the rotation center. If the evaluation function E(CP) used to evaluate the contrast of the reconstructed tomographic image is considered, when the position CP is made a variable, CP where the evaluation function E(CP) is made a maximum becomes the proper position CPp of the rotation center.

The method of obtaining a variable with which a predetermined function is made a maximum (or a minimum in some cases) is referred to as "the optimization" in the field of the numerical calculation, and thus is well known. Therefore, the automatic estimation of the position CP of the rotation-axis projection results in the problem of the optimization of the evaluation function E(CP). But, in general, it is known that the optimization which does not entail the error at all can not be carried out by the finite arithmetic operation. On the other hand, since in the X-ray detection, the error is contained in the imaged image data itself becoming the source of the optimization, in the present invention, the optimized value CPf=CPp is obtained within the range of the predetermined error e which is previously decided.

After completion of the formulation, the next problem is the optimization method and the method of calculating the evaluation function E(CP). As for the optimization method, the various kinds of methods have already been proposed in the field of the numerical calculation. Therefore, in the following description, the method of applying the well known optimization method and the evaluation function to the present invention will hereinbelow be described.

The simplest optimization method is the method wherein the reconstruction arithmetic operation is successively carried out while changing the position CP of the rotation axis projection from the initial value CP0 a small change amount dCP by a small change amount dCP; the evaluation function E(CP) for the resultant reconstructed image is calculated; and the position CP of the rotation-axis projection where the value of the evaluation function E(CP) becomes a maximum is decided as the optimized value CPf.

That is, when an arbitrary position of the rotation-axis projection is Cpi, and its evaluation function is Ei, the arbitrary position Cpi of the rotation-axis projection, when $i=0, 1, \ldots, n$ is expressed by (Expression 3).

$$Cpi = CP0 + I \times dCP \qquad \text{(Expression 3)}$$

Therefore, the evaluation function $Ei=E(Cpi)$ for each of $i=0, 1, \ldots, n$ is obtained, and the position Cpi where the evaluation function Ei becomes a maximum is obtained, whereby the optimized value CPf of the position of the rotation-axis projection is obtained. In this case, the position CP of the rotation-axis projection can not be estimated with higher accuracy than the change amount dCP. Then, the optimized value CPf of the position of the rotation-axis projection for the change amount dCP is temporarily estimated on the basis of the above-mentioned procedure. Next, the change amount of the position CP of the rotation-axis projection is newly obtained by (Expression 4), and the initial value thereof is obtained by (Expression 5).

$$DCP' = dCP/n \qquad \text{(Expression 4)}$$

$$CP0' = Cpi - dCP' \times n/2 \qquad \text{(Expression 5)}$$

Thereafter, similarly to the above-mentioned process, the value of the position CP of the rotation-axis projection is changed from the initial value CP0' the change amount dCP' by the change amount dCP' ((Expression 6)), the position Cpi' of the rotation-axis projection where the evaluation function E(Cpi') shows a maximum is obtained, and the resultant position Cpi' of the rotation-axis projection is decided as a new optimized value CPf'.

$$Cpi' = CP0' + i \times dCP' \qquad \text{(Expression 6)}$$

The same processing is repeatedly executed until the minute change amount of the position CP of the rotation-axis projection falls within the desired error, whereby the optimized value CPf of the position of the rotation-axis projection which has the desired accuracy can be obtained. But, in general, since the reconstruction arithmetic operation is expensive in calculation cost, i.e., it takes a lot of time to carry out the reconstruction arithmetic operation, it is better that the number of times of reconstruction arithmetic operation is small. Therefore, the optimized number of times of reconstruction arithmetic operation needs to be found out on the basis of the experimentation and the like.

(Evaluation Function)

Next, the method of calculating the evaluation function E(CP) will hereinbelow be described. As described above, when the position CP of the rotation-axis projection is deviated, the influence appears in which the artifact of arc shape is generated in the reconstructed image to reduce the contrast. By utilizing this property, there can be decided the evaluation function E(CP) which takes a maximum value (or a minimum value) when the value of the position CP of the rotation-axis projection becomes the proper value. Practically, not only the evaluation function E(CP) is simply decided, but also the imaging condition, the imaging object and the concern area to be reconstructed are suitably adjusted in such a way that the calculation of the evaluation function E(CP) becomes easy to be carried out, whereby it is possible to reduce a time required to estimate the geometry of the imaging system. But, in the following description, the concern area which is to be reconstructed and becomes an object of the evaluation is particularly referred to as "the evaluation area". In addition, in the present invention, the maximum value in the evaluation area which is obtained by the reconstruction is decided as the evaluation function E(CP) for the specific position CP of the rotation-axis projection.

In general, in the reconstructed image having high contrast, the maximum value in the reconstructed image becomes larger. Therefore, if the maximum value of the evaluation area is decided as the evaluation function E(CP), then it will show the value for which the fluctuations of the contrast are reflected. But, in the scope of claims of the present invention, it is to be understood that any of the functions which has a maximum value or a minimum value in the standard deviation, the mean value or the minimum value of the evaluation area, or the value which is calculated on the basis thereof, or the optimized value CPf may be decided as the evaluation function E(CP). In addition, it is also to be understood that the detection or the like of the artifact based on the image recognition is carried out, and on the basis of the detection result, the evaluation function E(CP) may be obtained.

In order to calculate the evaluation function E(CP), i.e., the contrast of the reconstructed image, it is not necessary to reconstruct the whole area for which the reconstructed arithmetic operation can be made, but only the specific area fulfilling the conditions which will be described later has only to be reconstructed. Therefore, in the present invention, the whole area for which the reconstruction arithmetic operation can be made is not decided as the evaluation area, but only the mid-plane cross section is decided as the evaluation area. In order to calculate the evaluation function E(CP), i.e., the contrast of the reconstructed image, the whole area for which the reconstruction arithmetic operation can be made does not need to be reconstructed, but only the specific area has only to be reconstructed. At this time, if only the reconstruction arithmetic operation for only the mid-plane cross section is carried out, then the operation volume required for the reconstruction arithmetic operation is kept to a minimum in terms of the property of the cone-beam reconstruction arithmetic operation by Feldkamp. In addition, since for the necessary projected image, only the projected image on the mid-plane projection has only to be require, the necessary pre-processing such as the gamma correction, the distortion correction, the logarithmic transformation and the non-uniformity correction is kept to a minimum. Therefore, it becomes possible to reduce largely a time required for the estimation of the geometry of the imaging means, and as a result it becomes possible to enhance the diagnostic efficiency.

(Other Estimate Operation for Position CP of Rotation-Axis Projection)

As for the optimization method of obtaining more efficiently the optimized position CP of the rotation-axis projection, the arithmetic operation method referred to as the well known "Brent method" can be used. "The Brent method" is realized by combining the arithmetic operation method referred to as "the golden section means" and the arithmetic operation method referred to as "the parabolic interpolation means" with each other and thus is the optimization method wherein the optimized value, i.e., the position CP where the evaluation function E(CP) shows a maximum value can be obtained with the less operation volume. The golden section means is the method wherein the range in which the presence of the optimized value is estimated is successively, surely narrowed. On the other hand, the parabolic interpolation means is the method wherein the work of applying a parabola to the given three points to obtain the vertex of the parabola to further apply a parabola to the resultant vertex and the two points of the given three points is repeatedly carried out to obtain the optimized value at high speed. While the optimized value can be found out more speedily in the parabolic interpolation means than in the golden section means, the parabolic interpolation means may not be applied depending on the condition in some cases.

The Brent method is the practical method in which the golden section means and the parabolic interpolation means are combined with each other. With respect to the details of the Brent method, for example, refer to an article of Willam H. Press et al.: "NUMERICAL RECIPES IN C", Cambridge University Press, Second Edition, pp. 402 to 405 (1992) ("NUMERICAL RECIPE IN C" Japanes version by Gijyutsu hyoron sha, pp. 289 to 292 (1993)) or the like. Of course, it is to be understood that any of the optimization methods other than the above-mentioned methods may be utilized in order to obtain the optimized value CPf.

(Procedure of Reconstructing Three-dimensional X-ray Absorption Coefficient Distribution Image)

Next, the description will hereinbelow be given with respect to the procedure of obtaining the X-ray absorption coefficient distribution image, i.e., the reconstructed image by utilizing the position CP of the rotation-axis projection which is estimated as described above. First of all, it is assumed that the necessary pre-processing in this stage, i.e., the gamma correction, the distortion correction, the logarithmic transformation and the non-uniformity correction for the imaged image data are carried out to obtain all of the projected images. Then, the reconstruction arithmetic operation is carried out on the basis of all of the projected images to obtain the reconstructed image. As for the reconstruction arithmetic operation processing therefore, there is known the cone-beam reconstruction arithmetic operation method by Feldkamp described in the article 1.

The description will hereinbelow be given on the basis of the geometry of the imaging system shown in FIG. 3. While in the reconstruction arithmetic operation described in the article 1, the arithmetic operation is carried out on the basis of a projection angle a, the coordinate (u, v) on the projection plane, and the coordinate (x, y, z) in the reconstruction space, the correspondence relationship between these coordinates and the projected image obtained from the imaged imageing data which is actually imaged must be clear because the above-mentioned projected image actually obtained is the discretely sampled data.

The ideal projected image is expressed in the form of P(a, u, v) by employing the projection angle a and the position u, v on the projection plane. On the other hand, the actually obtained projected image is decided as Pr{I, j, k}. Since the latter projected image is discretely sampled, the indexes i, j and k take the integral numbers of i=0, 1, . . . , N-1, j=0, 1, . . . , M-1 and k=0, 1, . . . , L-1, respectively. Also, N means the number of projections, and M and N mean the resolution in the direction of u, and the resolution in the direction v, respectively. In actual, this projected image corresponds to the data stored in the specific location on a memory which is specified by the indexes i, j and k. At this time, the following relationship of (Expression 7) is established between P(a, u, v) and Pr{i, j, k}. But, a function Int(x) in (Expression 7) is a function of omitting the figures of x below the decimal point.

$$P(a, u, v)=Pr\{nt(a/dA), Int(u+CP)/dU, Int((v+MP)/dV)\}$$ (Expression 7)

From this (Expression 7), the coordinates used in the reconstruction arithmetic operation and the discretely sampled projected image obtained from the actual imaged image data is established. In the reconstruction arithmetic operation, the discretely sampled projected image may be utilized on the basis of (Expression 7). Of cause, the reconstruction arithmetic operation method from the projected image is not intended to be limited to only the reconstruction arithmetic operation method by Feldkamp described in the article 1. However, no matter what reconstruction arithmetic operation method we may employ, the geometry of the imaging means is the basis of the arithmetic operation, and hence it remains unchanged that the correspondence relationship between the projected image which was obtained from the actual imaged image data and the coordinates in the reconstruction arithmetic operation is established.

As described above, in the cone-beam X-ray CT of the embodiment 1, there is utilized the fact that since if the reconstruction arithmetic operation is carried out in the state in which the position of the rotation-axis projection 17 projected on the projection plane 15 is deviated, then the artifact of arc shape is generated in the resultant reconstructed image, the contrast is reduced. That is, first of all, the mid-plane reconstruction means 26 carries out the reconstruction of the reconstructed image with the value decided by the initial-value decision means 25 as the initial value of the position of the rotation-axis projection, and then the evaluation-function calculation means 28 calculates the evaluation function E(CP0) corresponding to the contrast of the reconstructed image. Next, the optimizing means 29 updates the initial value of the position of the rotation-axis projection, the mid-lane reconstructed image based on the updated value of the position of the rotation-axis projection, the evaluation-function calculation means 28 calculates the evaluation function E(CP1) corresponding to the contrast of the reconstructed image in the updated value of the position of the rotation-axis projection, and the optimizing means compares the evaluation functions E(CP0) and E(CP1) with each other. Then, the above-mentioned operation is repeatedly carried out to calculate the position of the rotation-axis projection 17 where the contrast becomes a maximum, whereby it is possible to obtain the proper position CPp of the rotation-axis projection. As a result, the rotation-axis projection 17 as the parameter used to define the geometry of the imaging system can be automatically estimated independently of a sense of an operator by using the value which is independent of a sense of an operator as the contrast of the reconstructed image. Therefore, a time required for the estimation of the geometry of the imaging system, i.e., a time required to adjust the X-ray CT can be reduced and hence the diagnostic efficiency can be enhanced. In addition, since the parameter used to define the geometry of the imaging system can be automatically estimated independently of a sense of an operator, the position of the rotation-axis projection which contributes greatly to the promotion of the high image quality of the reconstructed image can be obtained with high accuracy.

EMBODIMENT 2

Figure 5:
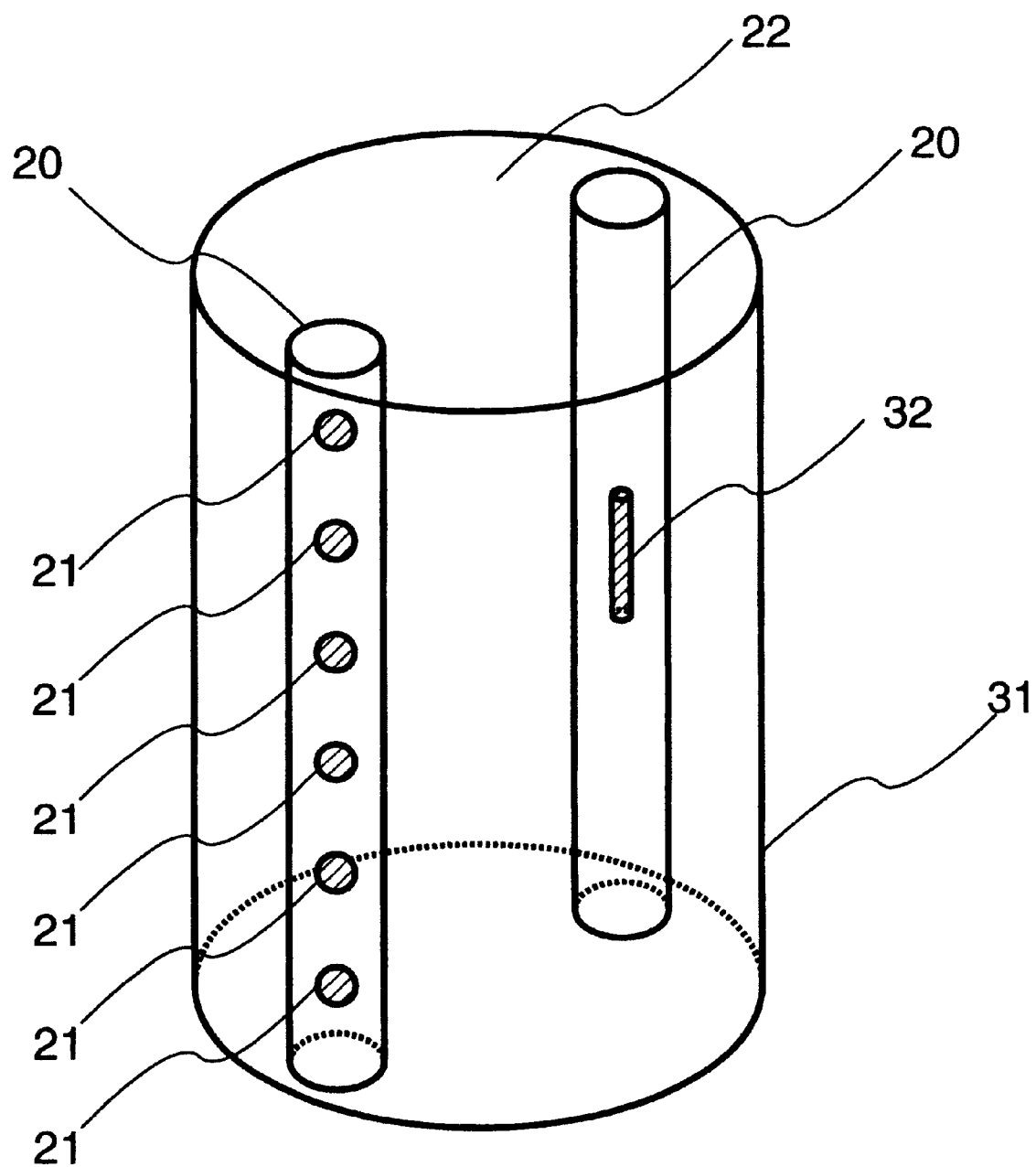
FIG. 5 is a view useful in explaining the schematic construction of a position estimate phantom of the rotation axis projection used in estimation of the geometry of the imaging system in a cone-beam X-ray CT of an embodiment 2 of the present invention.
Figure 6:
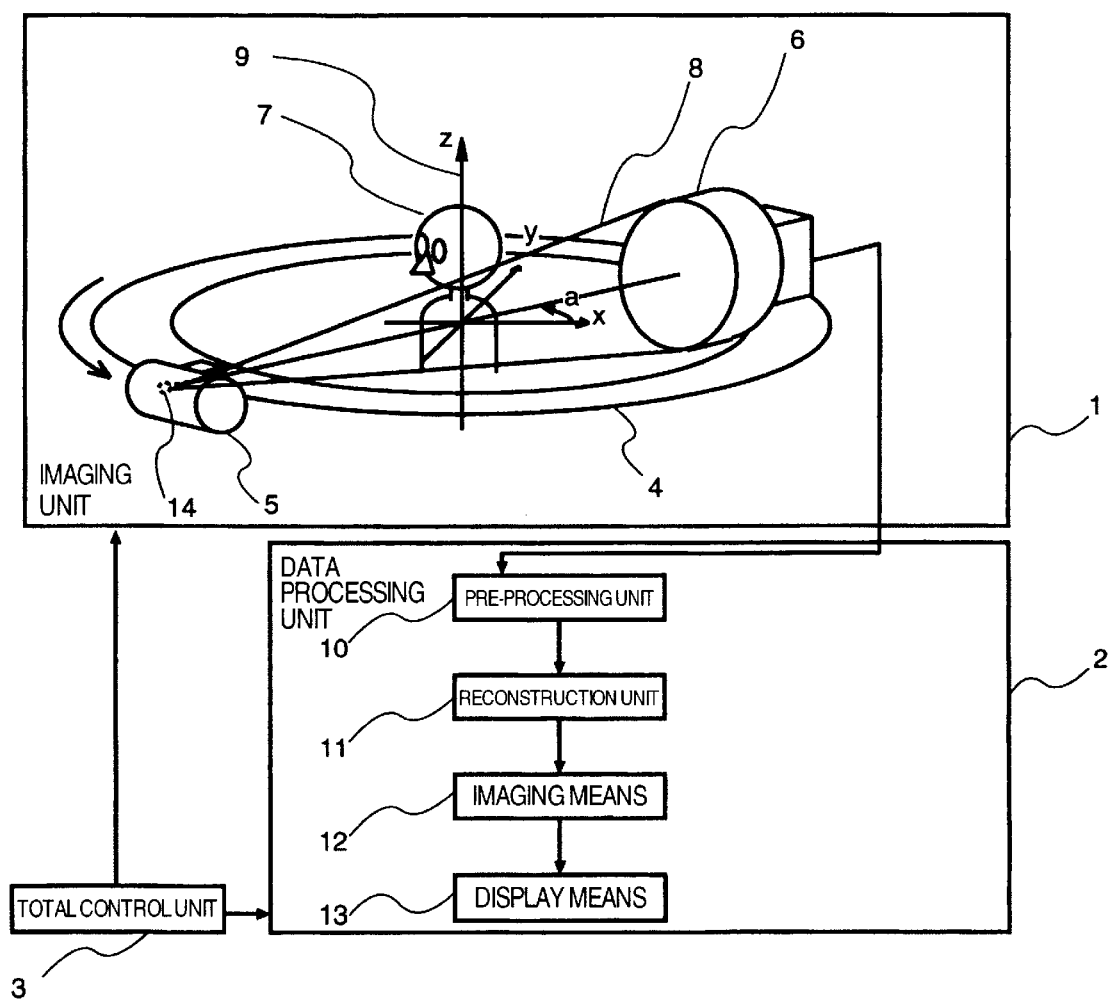
FIG. 6 is a view showing the schematic construction of a conventional cone-beam X-ray CT.

FIG. 5 is a view useful in explaining the schematic construction of the phantom for use in the estimation of the geometry of the imaging system in a cone-beam X-ray CT of an embodiment 2. In the embodiment 1 employing the phantom 31 shown in FIG. 2, the detection for the estimation of the position of the mid-plane projection, and the detection for the estimation of the position of the rotation-axis projection must be carried out separately from each other. On the other hand, the embodiment 2 relates to the phantom for concluding the detection for the estimation of the position of the mid-plane projection and the detection for the estimation of the position of the rotation-axis projection by one time.

Figure 7:
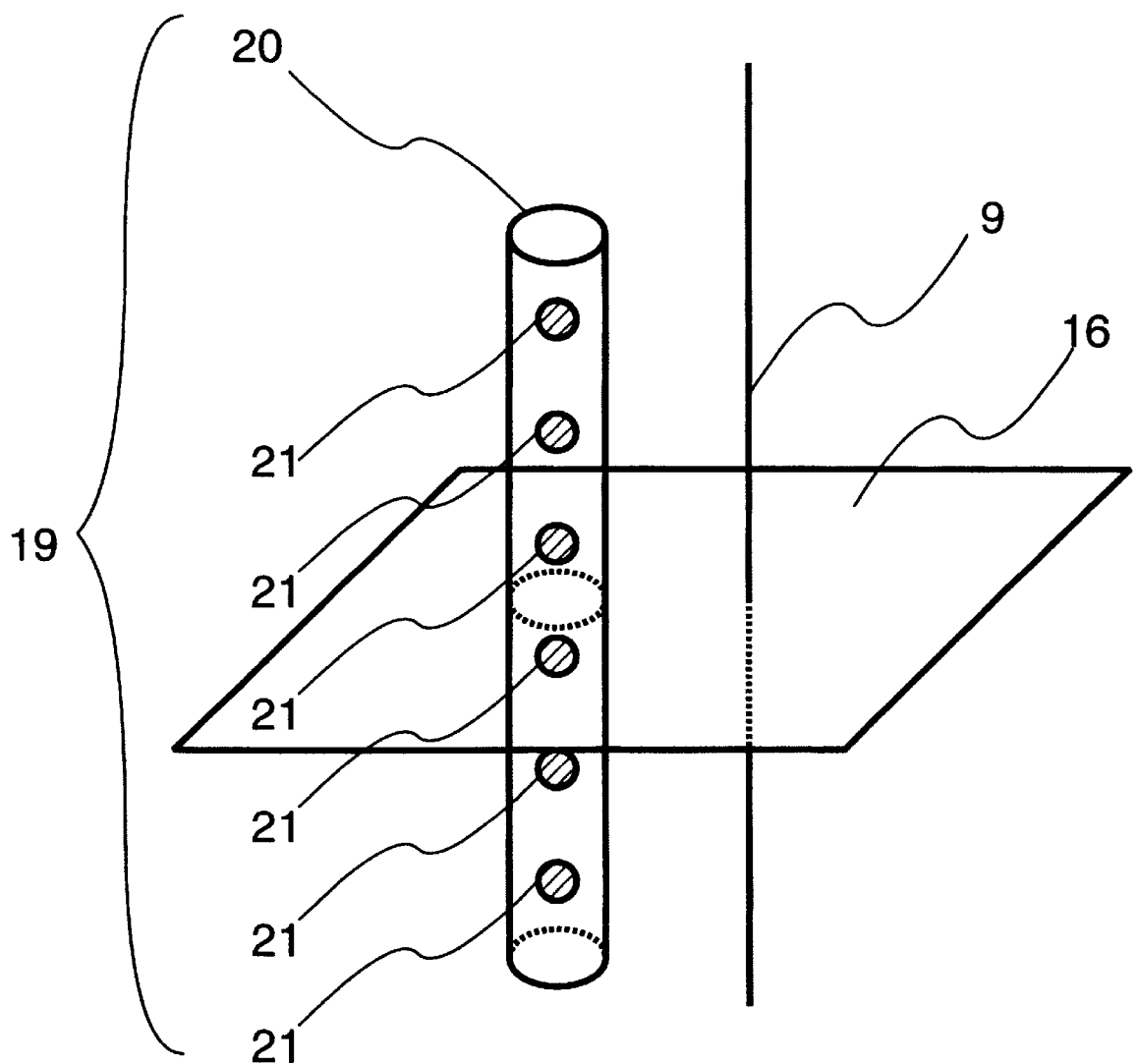
FIG. 7 is a view useful in explaining the schematic construction of a conventional phantom.
Figure 8:
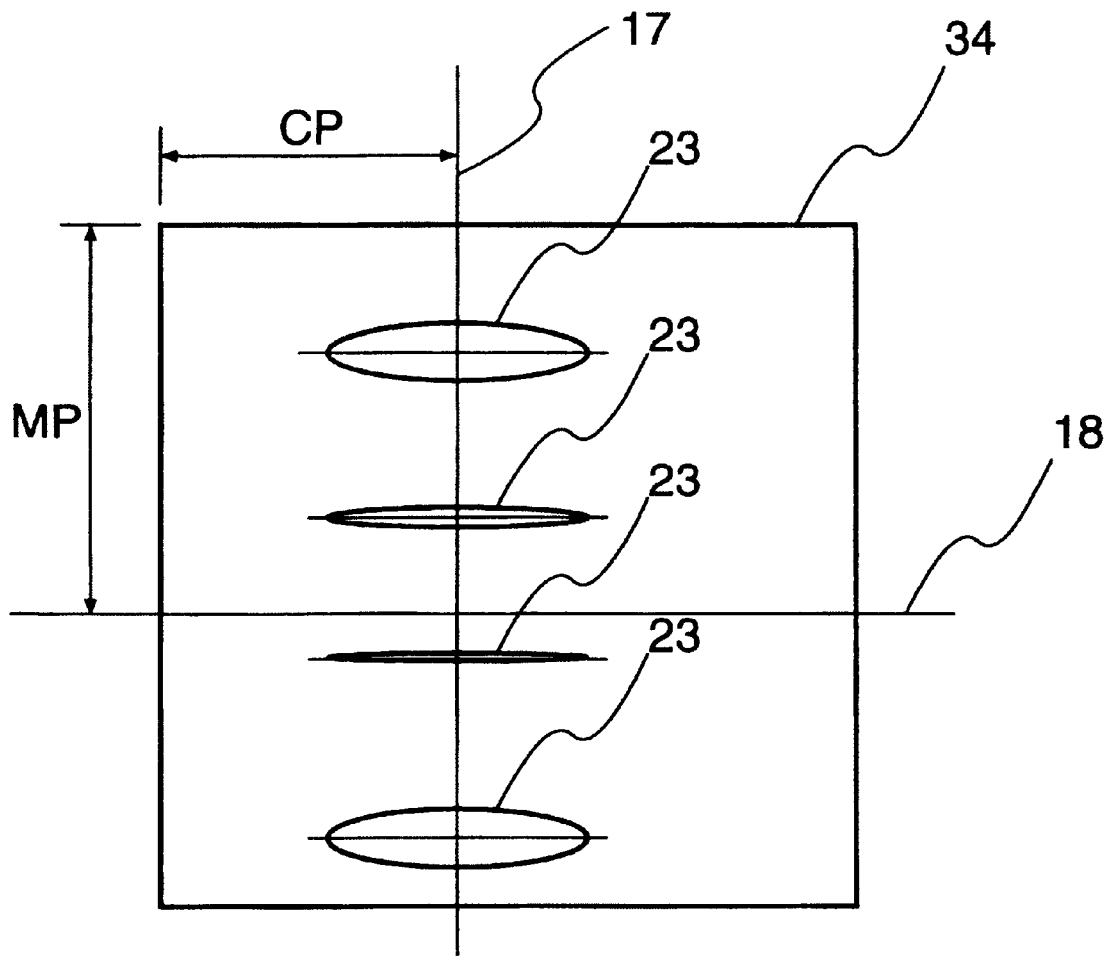
FIG. 8 is a view useful in explaining the procedure of estimating the geometry of an imaging system by the conventional cone-beam X-ray CT.

In FIG. 5, reference numeral 20 designates a support member, reference numeral 21 designates a corpuscle-shaped high absorption member, reference numeral 32 designates an insert, and reference numeral 31 designates a body of a phantom. As shown in FIG. 5, the phantom 31 of the embodiment 2 is such that the phantom, shown in FIG. 2, in which the insert 32 made of the material having the high X-ray absorption is embedded in the support member 20 having the low X-ray absorption (hereinafter, referred to as "the first phantom" for short, when applicable), and the phantom, shown in FIG. 7, in which the corpuscle-shaped high absorption members 21 each having the diameter of about 1 mm to about 2 mm each of which is made of the material having the high X-ray absorption are embedded at the intervals of about 2 cm in the support member 20 having the low X-ray absorption along the axial direction of the support member 20 (hereinafter, referred to as "the second phantom" for short, when applicable) are fixed with a second support member 22. But, the phantom 31 shown in FIG. 5 is also claimed by the present invention.

The support member 20 is formed into a stick made of a material having a small X-ray absorption coefficient such as a plastic material or polymeric resin including acrylate resin, vinyl chloride, polycarbonate or the like, or a material, typified by wood, through which the X-ray is transmitted and which has the high strength against the mechanical destruction. The corpuscle-shaped high absorption member 21 is made of a material having the high X-ray absorption coefficient such as tungsten, platinum or an iron-nickel-chromium series alloy. As for the number of corpuscle-shaped high absorption members 21, for example, two or more is required. In addition, while the positions of the corpuscle-shaped high absorption members 21 are arbitrary as long as they are arranged along the axis of the support member 20, the corpuscle-shaped high absorption members 21 are arranged in such a way that when the phantom 31 is installed in such a way that at least the insert 32 crosses the mid-plane 16, at least two corpuscle-shaped high absorption members 21 are arranged so as to sandwich therebetween the mid-plane 16, whereby the geometry of the imaging system can be carried out with one detection of the transmitted X-ray image made around the object. The insert 32 is the columnar body with a predetermined length which is made of a material having large X-ray absorption coefficient such as tungsten, platinum or an iron-nickel-chromium series alloy, and is formed into a wire or a stick. Similarly to the support member 20, the second support member 22 is formed into a stick made of a material having a small X-ray absorption coefficient such as a plastic material or a polymeric resin including acrylate resin, vinyl chloride, polycarbonate or the like, or a material, typified by wood, through which the X-ray is transmitted and which has the high strength against the mechanical destruction. In the cone-beam X-ray CT in the embodiment 2, by employing the second phantom as described above, the estimation of the position MP of the mid-plane projection and the estimation of the position CP of the rotation-axis projection can be continuously carried out on the basis of the imaged data obtained by one detection. The estimation of the position MP of the mid-plane projection is as shown in the prior art method.

As described above, in the cone-beam X-ray CT apparatus of the embodiment 2, there is offered the effect that the transmitted X-ray image which is obtained around the object by employing the phantom 31 shown in FIG. 5 is detected, whereby next to the estimation of the position MP of the mid-plane projection, the estimation of the position CP of the rotation axis projection can be continuously carried out from the imaged data obtained one and the same detection of the phantom.

The X-ray CT of each of the embodiments 1 and 2 may include the mid-plane projection memory means 30 as the memory means (temporary storage means) for storing a part of the projected image which has been subjected to the processing by the pre-processing means 10 for a period of time when executing the geometry estimate processing. Since the projected image required for the geometry estimation may be only the part corresponding to the mid-plane projection 18, for example, the memory means employing the well known semiconductor memory is prepared, as the memory means from which the data can be read out at high speed, in the form of the mid-plane projection memory means 30, separately from the memory means for storing therein the whole projected image, whereby the mid-plane reconstruction can be carried out speedily. As a result, a time required for the estimation of the geometry of the imaging system can be further reduced.

As the two-dimensional detector 6, there is used the X-ray image intensifier-TV camera system or the two-dimensional X-ray detector in which the photodiodes, the TFT switches and the like are arranged in a two-dimensional manner. In addition, in particular, in the case where the present invention is applied to the medical care X-ray CT in which the human body is treated as the detection object as the object, the effect inherent therein can be obtained. In this case, since the high image quality of the X-ray tomographic image or/and the three-dimensional X-ray image which is/are obtained can be realized, the discovery of the relatively small tumors or the like such as the early cancer becomes easy, and hence the diagnostic accuracy as well as the diagnostic efficiency can be enhanced. But, it is to be understood that as typified by the goods, in the case where any of the things other than the human body is treated as the object, the present invention can also be applied thereto.

From the foregoing, it is to be understood that the present invention is not intended to be limited to the embodiments thereof and hence may be variously changed without departing from the object matter of the invention.

The meanings of the reference numerals used in the description of the drawings are as follows: 1: imaging unit, 2: image processing unit, 3: control unit, 4: scanner (rotating disc), 5: X-ray source, 6: two dimensional detector, 7: object, 8: X-ray beam, 9: rotation center, 10: pre-processing means, 11: reconstruction means, 12: imaging means, 13: display means, 14: X-ray focus, 15: projection plane, 16: mid-plane, 17: rotation-axis projection, 18: mid-plane projection, 19: geometry phantom, 20: support member, 21: corpuscle-shaped high absorption member, 22: second support member, 23: elliptical locus, 24: geometry estimate means, 25: initial-value decision means, 26: mid-plane reconstruction means, 27: evaluation-area decision means, 28: evaluation-function calculation means, 29: optimizing means, 30: mid-plane projection memory means, 31: phantom, 32: insert, 34: added image.

What is claimed is:

1. An X-ray CT apparatus comprising: a scanner mounted with a detection system having an X-ray source for generating X-rays applied radially to an object and detection means arranged so as to be opposite to said X-ray source and adapted to detect the image of the transmitted X-rays transmitted through said object; rotation means for rotating said scanner around said object; reconstruction means for reconstructing a three-dimensional X-ray absorption coefficient distribution image of said object from said transmitted X-ray image; decision means for deciding the rotation-axis projection position which is the position where the rotation center of said scanner is projected on the detection plane of a two-dimensional sensor constituting said X-ray absorption coefficient distribution image reconstructed by using said rotation-axis projection position decided by said decision means, said rotation-axis projection position is estimated; an X-ray tomographic image or/and a three-dimensional X-ray image of said object is generated from said three-dimensional X-ray absorption coefficient distribution image reconstructed by said reconstruction means in said estimated rotation-axis projection position; and the X-ray tomographic image or/and the three-dimensional X-ray image of said object is/are displayed.

2. An X-ray CT apparatus according to claim 1, wherein said transmitted X-ray image is the image which is obtained by installing a phantom in the vicinity of the rotation center of said scanner in order to detect said phantom; said phantom includes a columnar body which has the axial direction roughly in the same direction as that of the rotation center of said scanner, and a support member for holding said columnar body formed into a column-like shape; and the X-ray absorption coefficient of said columnar body is larger than that of said support member.

3. An X-ray CT apparatus comprising: a scanner mounted with a detection system having an X-ray source for generating X-rays applied radially to an object and detection means arranged so as to be opposite to said X-ray source and adapted to detect the image of the transmitted X-rays transmitted through said object; rotation means for rotating said scanner around said object; reconstruction means for reconstructing a three-dimensional X-ray absorption coefficient distribution image of said object from said transmitted X-ray image; and estimate means for estimating the rotation-axis projection position on the basis of the X-ray absorption coefficient distribution image which is reconstructed by changing said rotation-axis projection position as the position of the rotation center of said scanner projected on a detection plane of a two-dimensional detector constituting said detection means.

4. An X-ray CT apparatus according to claim 3, wherein said estimate means includes: initial-value decision means for deciding an initial value of said rotation-axis projection position; partial reconstruction means for on the basis of said rotation-axis projection position decided by said initial-value decision means, reconstructing a part of said X-ray absorption coefficient distribution image; and evaluation-function calculation means for evaluating the contrast of said X-ray absorption coefficient distribution image reconstructed by said partial reconstruction means to obtain a value of an evaluation function; and optimizing means for on the basis of the value of said evaluation function which is obtained by changing said rotation-axis projection position, estimating said rotation-axis projection position.

5. An X-ray CT apparatus according to claim 4, wherein said initial-value decision means decides as said initial value the position at the center of an aperture width of a two-dimensional detector constituting said detection means, said aperture width corresponding to a rotation tangential direction of said scanner.

6. An X-ray CT apparatus according to claim 4, wherein said partial reconstruction means reconstructs said X-ray absorption efficient distribution image on a rotation orbit plane of said X-ray source from said transmitted X-ray image.

7. An X-ray CT apparatus according to claim 4, wherein said evaluation function is a maximum value of the CT value within a predetermined area of said X-ray absorption coefficient distribution image, and wherein said apparatus further comprises: rendering means for generating an X-ray tomographic image or/and a three-dimensional X-ray image of said object from said three-dimensional X-ray absorption coefficient distribution image which is reconstructed in said rotation-axis projection position where said evaluation function shows a maximum; and display means for displaying the X-ray tomographic image or/and the three-dimensional X-ray image of said object.

8. An X-ray CT apparatus according to claim 4, wherein said evaluation function is a difference between a maximum value and a minimum value of the CT value within a predetermined area of said X-ray absorption coefficient distribution image, and wherein said apparatus further comprises: imaging means for generating an X-ray tomographic image or/and a three-dimensional X-ray image of said object from said three dimensional X-ray absorption coefficient distribution image which is reconstructed in said rotation-axis projection position where said evaluation function shows a maximum; and display means for displaying the X-ray tomographic image or/and the three-dimensional X-ray image of said object.

9. An X-ray CT apparatus according to claim 4, further comprising evaluation-area decision means for specifying a pixel position where the CT value in said X-ray absorption coefficient distribution image reconstructed by said partial reconstruction means becomes a maximum or a local maximum, wherein said optimizing means estimates said rotation-axis projection position from the area containing said pixel position.

10. An X-ray CT apparatus according to claim 4, further comprising: pre-processing means for carrying out the pre-processing for said transmitted X-ray image on the rotation orbit plan of said X-ray source; and temporary storage means for storing said transmitted X-ray image which has been subjected to the pre-processing by said pre-processing means for a period of time when said rotation-axis projection position is estimated.

11. A phantom for use in an X-ray CT apparatus defined in any one of claims 1 and 3 to 10, wherein a phantom is provided which comprises a columnar body which has the axial direction roughly in the same direction as that of the rotation center of said scanner and a support member for holding said columnar body which is formed into a columnar shape, and wherein the X-ray absorption coefficient of said columnar body is larger than that of said support member.

12. An X-ray detecting method comprising: the steps of utilizing a scanner mounted with a detection system having an X-ray source for generating X-rays applied radially to an object and detection means arranged so as to be opposite to said X-ray source, collecting images of transmitted X-rays transmitted through said object; deciding previously the rotation-axis projection position which is the position where the rotation center of said scanner is projected on the detection plane of a two-dimensional detector constituting said detection means; on the basis of said rotation-axis projection position, reconstructing the X-ray absorption coefficient distribution image of said object from said transmitted X-ray image; specifying said rotation-axis projection position, where the contrast of said X-ray absorption coefficient distribution image becomes a maximum or a local maximum, as said rotation-axis projection position on said transmitted X-ray image; on the basis of said specified rotation axis projection position, reconstructing the three-dimensional X-ray absorption coefficient distribution image of said object from said transmitted X-ray image; generating the X-ray tomographic image or/and the three-dimensional X-ray image from said three-dimensional X-ray absorption coefficient distribution image; and displaying the X-ray tomographic image or/and the three-dimensional X-ray image of said object.

13. An X-ray detecting method comprising: the steps of utilizing a scanner mounted with a detection system having an X-ray source for generating X-rays applied radially to an object and detection means arranged so as to be opposite to said X-ray source, collecting images of transmitted X-rays transmitted through said object; deciding previously the rotation-axis projection position which is the position where the rotation center of said scanner is projected on the detection plane of a two-dimensional detector constituting said detection means; on the basis of said rotation-axis projection position, reconstructing the X-ray absorption coefficient distribution image of said object from said transmitted X-ray image; estimating said rotation-axis projection position from said X-ray absorption coefficient distribution image; on the basis of said estimated rotation-axis projection position, reconstructing the three-dimensional X-ray absorption coefficient distribution image of said object from said transmitted X-ray image; generating the X-ray tomographic image or/and the three-dimensional X-ray image from said three-dimensional X-ray absorption coefficient distribution image; and displaying the X-ray tomographic image or/and the three-dimensional X-ray image of said object.

* * * * *